United States Patent
Afzal

(10) Patent No.: US 9,687,353 B2
(45) Date of Patent: Jun. 27, 2017

(54) PROSTHETIC INTERVERTEBRAL DISCS HAVING BALLOON-BASED FILLABLE CORES THAT ARE IMPLANTABLE BY MINIMALLY INVASIVE SURGICAL TECHNIQUES

(75) Inventor: Thomas A. Afzal, Menlo Park, CA (US)

(73) Assignee: SPINAL KINETICS, INC.

( * ) Notice: Subject to any disclaimer, the term of this patent is extended or adjusted under 35 U.S.C. 154(b) by 1269 days.

(21) Appl. No.: 12/060,191

(22) Filed: Mar. 31, 2008

(65) Prior Publication Data

US 2009/0076610 A1 Mar. 19, 2009

Related U.S. Application Data

(60) Provisional application No. 60/909,443, filed on Mar. 31, 2007.

(51) Int. Cl.
*A61F 2/44* (2006.01)
*A61F 2/30* (2006.01)

(52) U.S. Cl.
CPC .............. *A61F 2/442* (2013.01); *A61F 2/441* (2013.01); *A61F 2002/30075* (2013.01); *A61F 2002/30461* (2013.01); *A61F 2002/30556* (2013.01); *A61F 2002/30581* (2013.01); *A61F 2002/30583* (2013.01); *A61F 2002/30586* (2013.01); *A61F 2002/30784* (2013.01); *A61F 2002/30884* (2013.01); *A61F 2002/448* (2013.01); *A61F 2002/4495* (2013.01); *A61F 2210/0061* (2013.01); *A61F 2210/0085* (2013.01); *A61F 2220/0075* (2013.01); *A61F 2250/0009* (2013.01)

(58) Field of Classification Search
USPC ......... 623/17.11, 17.12, 17.13, 17.14, 17.15, 623/17.16
See application file for complete search history.

(56) References Cited

U.S. PATENT DOCUMENTS

| | | | |
|---|---|---|---|
| 3,867,728 A * | 2/1975 | Stubstad et al. | ........... 623/17.16 |
| 4,932,969 A | 6/1990 | Frey et al. | |
| 5,071,437 A | 12/1991 | Steffee | |
| 5,171,281 A | 12/1992 | Parsons et al. | |
| 5,192,326 A * | 3/1993 | Bao et al. | ................... 623/17.12 |
| 5,370,697 A | 12/1994 | Baumgartner | |
| 6,626,943 B2 | 9/2003 | Eberlin et al. | |
| 6,645,248 B2 | 11/2003 | Casutt | |
| 6,733,532 B1 | 5/2004 | Gauchet et al. | |
| 7,563,284 B2 | 7/2009 | Coppes et al. | |
| 2004/0133280 A1* | 7/2004 | Trieu | .......................... 623/17.16 |
| 2005/0027364 A1* | 2/2005 | Kim et al. | .................. 623/17.13 |
| 2005/0033437 A1* | 2/2005 | Bao et al. | .................. 623/17.15 |

(Continued)

OTHER PUBLICATIONS

U.S. Appl. No. 60/403,356, filed Aug. 15, 2002.

(Continued)

*Primary Examiner* — Zade Coley
(74) *Attorney, Agent, or Firm* — E. Thomas Wheelock

(57) ABSTRACT

The described devices are spinal implants that may be surgically implanted into the spine to replace damaged or diseased discs using a posterior approach. The discs are prosthetic devices that approach or mimic the physiological motion and reaction of the natural disc.

27 Claims, 4 Drawing Sheets

(56) References Cited

U.S. PATENT DOCUMENTS

2005/0228500 A1* 10/2005 Kim et al. ............... 623/17.13

OTHER PUBLICATIONS

U.S. Appl. No. 60/403,402, filed Aug. 15, 2002.

Spinal Kinetics, Inc.'s Preliminary Invalidity Contentions (USDC, Case No. 5:09-cv-01201, *Synthes USA et al.* v. *Spinal Kinetics, Inc.*, Sep. 8, 2009).

Spinal Kinetics, Inc.'s Preliminary Invalidity Contentions—Exhibit 1 (chart comparing claims of U.S. Pat. No. 7,429,270 to Stubstad U.S. Pat. No. 3,867,728).

Spinal Kinetics, Inc.'s Preliminary Invalidity Contentions—Exhibit 2 (chart comparing claims of U.S. Pat. No. 7,429,270 to Baumgartner U.S. Pat. No. 5,370,697 in view of Stubstad U.S. Pat. No. 3,867,728 and Steffee U.S. Pat. No. 5,071,437).

Spinal Kinetics, Inc.'s Preliminary Invalidity Contentions—Exhibit 3 (chart comparing claims of U.S. Pat. No. 7,429,270 to Baumgartner U.S. Pat. No. 5,370,697 in view of Stubstad U.S. Pat. No. 3,867,728 and Parsons U.S. Pat. No. 5,171,281).

Spinal Kinetics, Inc.'s Preliminary Invalidity Contentions—Exhibit 4 (chart comparing claims of U.S. Pat. No. 7,429,270 to Baumgartner U.S. Pat. No. 5,370,697 in view of Stubstad U.S. Pat. No. 3,867,728 and Eberlein U.S. Pat. No. 6,626,943).

Spinal Kinetics, Inc.'s Preliminary Invalidity Contentions—Exhibit 5 (chart comparing claims of U.S. Pat. No. 7,429,270 to Baumgartner U.S. Pat. No. 5,370,697 in view of Stubstad U.S. Pat. No. 3,867,728 and Casutt U.S. Pat. No. 6,645,248).

Spinal Kinetics, Inc.'s Preliminary Invalidity Contentions—Exhibit 6 (chart comparing claims of U.S. Pat. No. 7,429,270 to Baumgartner U.S. Pat. No. 5,370,697 in view of Stubstad U.S. Pat. No. 3,867,728 and Frey U.S. Pat. No. 4,932,969).

Spinal Kinetics, Inc.'s Preliminary Invalidity Contentions—Exhibit 7 (chart comparing claims of U.S. Pat. No. 7,429,270 to Baumgartner U.S. Pat. No. 5,370,697 in view of Stubstad U.S. Pat. No. 3,867,728 and Gauchet U.S. Pat. No. 6,733,532).

Spinal Kinetics, Inc.'s Preliminary Invalidity Contentions—Exhibit 8 (chart comparing claims of U.S. Pat. No. 7,429,270 to Baumgartner U.S. Pat. No. 5,370,697 in view of Stubstad U.S. Pat. No. 3,867,728 and Development and Characterization of a Prosthetic Intervertebral Disc, Robert Hudgins, Georgia Inst. of Tech., Nov. 1998).

Spinal Kinetics, Inc.'s Preliminary Invalidity Contentions—Exhibit 9 (chart comparing claims of U.S. Pat. No. 7,429,270 to Stubstad U.S. Pat. No. 3,867,728 in view of Baumgartner U.S. Pat. No. 5,370,697).

Spinal Kinetics, Inc.'s Preliminary Invalidity Contentions—Exhibit 10 (chart comparing claims of U.S. Pat. No. 7,429,270 to Baumgartner U.S. Pat. No. 5,370,697 in view of Stubstad U.S. Pat. No. 3,867,728 and Steffe U.S. Pat. No. 4,071,437).

Spinal Kinetics, Inc.'s Preliminary Invalidity Contentions—Exhibit 11 (chart comparing claims of U.S. Pat. No. 7,429,270 to Baumgartner U.S. Pat. No. 5,370,697 in view of Stubstad U.S. Pat. No. 3,867,728 and Casutt U.S. Pat. No. 6,645,248).

Spinal Kinetics, Inc.'s Preliminary Invalidity Contentions—Exhibit 12 (chart comparing claims of U.S. Pat. No. 7,429,270 to Stubstad U.S. Pat. No. 3,867,728 in view of Development and Characterization of a Prosthetic Intervertebral Disc, Robert Hudgins, Georgia Inst. of Tech., Nov. 1998).

Spinal Kinetics, Inc.'s Preliminary Invalidity Contentions [Amended] (USDC, Case No. 5:09-cv-01201, *Synthes USA et al.* v. *Spinal Kinetics, Inc.*, Dec. 28, 2009).

Spinal Kinetics, Inc.'s Preliminary Invalidity Contentions [Amended]—Exhibit 1 (chart comparing claims of U.S. Pat. No. 7,429,270 to Stubstad U.S. Pat. No. 3,867,728).

Spinal Kinetics, Inc.'s Preliminary Invalidity Contentions [Amended]—Exhibit 2 (chart comparing claims of U.S. Pat. No. 7,429,270 to Coppes U.S. Pat. No. 7,563,284).

Spinal Kinetics, Inc.'s Preliminary Invalidity Contentions [Amended]—Exhibit 3 (chart comparing claims of U.S. Pat. No. 7,429,270 to Coppes U.S. Pat. No. 7,563,284 in combination with Stubstad U.S. Pat. No. 3,867,728).

Spinal Kinetics, Inc.'s Preliminary Invalidity Contentions [Amended]—Exhibit 4 (chart comparing claims of U.S. Pat. No. 7,429,270 to Baumgartner U.S. Pat. No. 5,370,697 in view of Stubstad U.S. Pat. No. 3,867,728 and Steffee U.S. Pat. No. 5,071,437).

Spinal Kinetics, Inc.'s Preliminary Invalidity Contentions [Amended]—Exhibit 5 (chart comparing claims of U.S. Pat. No. 7,429,270 to Baumgartner U.S. Pat. No. 5,370,697 in view of Stubstad U.S. Pat. No. 3,867,728 and Parsons U.S. Pat. No. 5,171,281).

Spinal Kinetics, Inc.'s Preliminary Invalidity Contentions [Amended]—Exhibit 6 (chart comparing claims of U.S. Pat. No. 7,429,270 to Baumgartner U.S. Pat. No. 5,370,697 in view of Stubstad U.S. Pat. No. 3,867,728 and Eberlein U.S. Pat. No. 6,626,943).

Spinal Kinetics, Inc.'s Preliminary Invalidity Contentions [Amended]—Exhibit 7 (chart comparing claims of U.S. Pat. No. 7,429,270 to Baumgartner U.S. Pat. No. 5,370,697 in view of Stubstad U.S. Pat. No. 3,867,728 and Casutt U.S. Pat. No. 6,645,248).

Spinal Kinetics, Inc.'s Preliminary Invalidity Contentions [Amended]—Exhibit 8 (chart comparing claims of U.S. Pat. No. 7,429,270 to Baumgartner U.S. Pat. No. 5,370,697 in view of Stubstad U.S. Pat. No. 3,867,728 and Frey U.S. Pat. No. 4,932,969).

Spinal Kinetics, Inc.'s Preliminary Invalidity Contentions [Amended]—Exhibit 9 (chart comparing claims of U.S. Pat. No. 7,429,270 to Baumgartner U.S. Pat. No. 5,370,697 in view of Stubstad U.S. Pat. No. 3,867,728 and Gauchet U.S. Pat. No. 6,733,532).

Spinal Kinetics, Inc.'s Preliminary Invalidity Contentions [Amended]—Exhibit 10 (chart comparing claims of U.S. Pat. No. 7,429,270 to Baumgartner U.S. Pat. No. 5,370,697 in view of Stubstad U.S. Pat. No. 3,867,728 and Development and Characterization of a Prosthetic Intervertebral Disc, Hudgins, Georgia Inst. of Tech., Nov. 1998).

Spinal Kinetics, Inc.'s Preliminary Invalidity Contentions [Amended]—Exhibit 11 (chart comparing claims of U.S. Pat. No. 7,429,270 to Stubstad U.S. Pat. No. 3,867,728 in view of Baumgartner U.S. Pat. No. 5,370,697).

Spinal Kinetics, Inc.'s Preliminary Invalidity Contentions [Amended]—Exhibit 12 (chart comparing claims of U.S. Pat. No. 7,429,270 to Baumgartner U.S. Pat. No. 5,370,697 in view of Stubstad U.S. Pat. No. 3,867,728 and Steffee U.S. Pat. No. 4,071,437).

Spinal Kinetics, Inc.'s Preliminary Invalidity Contentions [Amended]—Exhibit 13 (chart comparing claims of U.S. Pat. No. 7,429,270 to Baumgartner U.S. Pat. No. 5,370,697 in view of Stubstad U.S. Pat. No. 3,867,728 and Casutt U.S. Pat. No. 6,645,248).

Spinal Kinetics, Inc.'s Preliminary Invalidity Contentions [Amended]—Exhibit 14 (chart comparing claims of U.S. Pat. No. 7,429,270 to Stubstad U.S. Pat. No. 3,867,728 in view of Development and Characterization of a Prosthetic Intervertebral Disc, Hudgins, Georgia Inst. of Tech., Nov. 1998).

Spinal Kinetics, Inc.'s Second Amended Preliminary Invalidity Contentions (USDC, Case No. 5:09-cv-01201, *Synthes USA et al.* v. *Spinal Kinetics, Inc.*, Sep. 30, 2010).

Spinal Kinetics, Inc.'s Second Amended Preliminary Invalidity Contentions—Exhibit 1 (chart comparing claims of U.S. Pat. No. 7,429,270 to Neuentwicklung eines Implantates für den totalen Bandschiebenersatz, Vorgelegt von: Adrian Burn und Daniel Baumgartner Im Rahmen des Studiums für "Maschinenbau und Vergahrenstechnik" an der Eidgenöossischen Technischen Hochschule Zürich, im Feb. 2002).

Spinal Kinetics, Inc.'s Second Amended Preliminary Invalidity Contentions—Exhibit 2 (chart comparing claims of U.S. Pat. No. 7,429,270 to Neuentwicklung eines lumbalen bewegungserhaltenden Bandscheibenimplantates, Feb. 25, 2002).

(56) References Cited

OTHER PUBLICATIONS

Spinal Kinetics, Inc.'s Second Amended Preliminary Invalidity Contentions—Exhibit 3 (chart comparing claims of U.S. Pat. No. 7,429,270 to Stubstad U.S. Pat. No. 3,867,728).
Spinal Kinetics, Inc.'s Second Amended Preliminary Invalidity Contentions—Exhibit 4 (chart comparing claims of U.S. Pat. No. 7,429,270 to Baumgartner PCT/CH2003/00247).
Spinal Kinetics, Inc.'s Second Amended Preliminary Invalidity Contentions—Exhibit 5 (chart comparing claims of U.S. Pat. No. 7,429,270 to Neuentwicklung eines Implantates für den totalen Bandschiebenersatz, Vorgelegt von: Adrian Burn und Daniel Baumgartner Im Rahmen des Studiums für "Maschinenbau und Vergahrenstechnik" an der Eidgenöossischen Technischen Hochschule Zürich, im Feb. 2002).
Spinal Kinetics, Inc.'s Second Amended Preliminary Invalidity Contentions—Exhibit 6 (chart comparing claims of U.S. Pat. No. 7,429,270 to Neuentwicklung eines Implantates für den totalen Bandschiebenersatz, Vorgelegt von: Adrian Burn und Daniel Baumgartner Im Rahmen des Studiums für "Maschinenbau und Vergahrenstechnik" an der Eidgenöossischen Technischen Hochschule Zürich, im Feb. 2002).
Spinal Kinetics, Inc.'s Second Amended Preliminary Invalidity Contentions—Exhibit 7 (chart comparing claims of U.S. Pat. No. 7,429,270 to Stubstad U.S. Pat. No. 3,867,728 in view of Eberlein U.S. Pat. No. 6,626,943).
Spinal Kinetics, Inc.'s Second Amended Preliminary Invalidity Contentions—Exhibit 8 (chart comparing claims of U.S. Pat. No. 7,429,270 to Stubstad U.S. Pat. No. 3,867,728 in view of Kim U.S. Pat. No. 7,153,325).
Spinal Kinetics, Inc.'s Second Amended Preliminary Invalidity Contentions—Exhibit 9 (chart comparing claims of U.S. Pat. No. 7,429,270 to Stubstad U.S. Pat. No. 3,867,728 in view of Optimal Design of Synthetic Intervertebral Disc Prosthesis Considering Nonlinear Mechanical Behavior, Kweon et al., Dec. 20, 2001).
Spinal Kinetics, Inc.'s Second Amended Preliminary Invalidity Contentions—Exhibit 10 (chart comparing claims of U.S. Pat. No. 7,429,270 to Stubstad U.S. Pat. No. 3,867,728 in view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions—Exhibit 11 (chart comparing claims of U.S. Pat. No. 7,429,270 to Coppes U.S. Pat. No. 7,563,284 to Stubstad U.S. Pat. No. 3,867,728).
Spinal Kinetics, Inc.'s Second Amended Preliminary Invalidity Contentions—Exhibit 12 (chart comparing claims of U.S. Pat. No. 7,429,270 to Coppes U.S. Pat. No. 7,563,284 in view of Eberlein U.S. Pat. No. 6,626,943).
Spinal Kinetics, Inc.'s Second Amended Preliminary Invalidity Contentions—Exhibit 13 (chart comparing claims of U.S. Pat. No. 7,429,270 to Coppes U.S. Pat. No. 7,563,284 in view of Kim U.S. Pat. No. 7,153,325).
Spinal Kinetics, Inc.'s Second Amended Preliminary Invalidity Contentions—Exhibit 14 (chart comparing claims of U.S. Pat. No. 7,429,270 to Coppes U.S. Pat. No. 7,563,284 in view of Optimal Design of Synthetic Intervertebral Disc Prosthesis Considering Nonlinear Mechanical Behavior, Kweon et al., Dec. 20, 2001).
Spinal Kinetics, Inc.'s Second Amended Preliminary Invalidity Contentions—Exhibit 15 (chart comparing claims of U.S. Pat. No. 7,429,270 to Coppes U.S. Pat. No. 7,563,284 in view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions—Exhibit 16 (chart comparing claims of U.S. Pat. No. 7,429,270 to Baumgartner U.S. Pat. No. 5,370,697 in view of Stubstad U.S. Pat. No. 3,867,728).
Spinal Kinetics, Inc.'s Second Amended Preliminary Invalidity Contentions—Exhibit 17 (chart comparing claims of U.S. Pat. No. 7,429,270 to Baumgartner U.S. Pat. No. 5,370,697 in view of Eberlein U.S. Pat. No. 6,626,943).
Spinal Kinetics, Inc.'s Second Amended Preliminary Invalidity Contentions—Exhibit 18 (chart comparing claims of U.S. Pat. No. 7,429,270 to Baumgartner U.S. Pat. No. 5,370,697 in view of Kim U.S. Pat. No. 7,153,325).
Spinal Kinetics, Inc.'s Second Amended Preliminary Invalidity Contentions—Exhibit 19 (chart comparing claims of U.S. Pat. No. 7,429,270 to Baumgartner U.S. Pat. No. 5,370,697 in view of Optimal Design of Synthetic Intervertebral Disc Prosthesis Considering Nonlinear Mechanical Behavior, Kweon et al., Dec. 20, 2001).
Spinal Kinetics, Inc.'s Second Amended Preliminary Invalidity Contentions—Exhibit 20 (chart comparing claims of U.S. Pat. No. 7,429,270 to Baumgartner U.S. Pat. No. 5,370,697 in view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions—Exhibit 21 (chart comparing claims of U.S. Pat. No. 7,429,270 to Gauchet U.S. Pat. No. 6,733,532 in view of Stubstad U.S. Pat. No. 3,867,728).
Spinal Kinetics, Inc.'s Second Amended Preliminary Invalidity Contentions—Exhibit 22 (chart comparing claims of U.S. Pat. No. 7,429,270 to Gauchet U.S. Pat. No. 6,733,532 in view of Eberlein U.S. Pat. No. 6,626,943).
Spinal Kinetics, Inc.'s Second Amended Preliminary Invalidity Contentions—Exhibit 23 (chart comparing claims of U.S. Pat. No. 7,429,270 to Gauchet U.S. Pat. No. 6,733,532 in view of Kim U.S. Pat. No. 7,153,325).
Spinal Kinetics, Inc.'s Second Amended Preliminary Invalidity Contentions—Exhibit 24 (chart comparing claims of U.S. Pat. No. 7,429,270 to Gauchet U.S. Pat. No. 6,733,532 in view of Optimal Design of Synthetic Intervertebral Disc Prosthesis Considering Nonlinear Mechanical Behavior, Kweon et al., Dec. 20, 2001).
Spinal Kinetics, Inc.'s Second Amended Preliminary Invalidity Contentions—Exhibit 25 (chart comparing claims of U.S. Pat. No. 7,429,270 to Gauchet U.S. Pat. No. 6,733,532 in view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions—Exhibit 26 (chart comparing claims of U.S. Pat. No. 7,429,270 to Baumgartner U.S. Pat. No. 5,370,697 in view of Stubstad U.S. Pat. No. 3,867,728).
Spinal Kinetics, Inc.'s Second Amended Preliminary Invalidity Contentions—Exhibit 27 (chart comparing claims of U.S. Pat. No. 7,429,270 to Coppes U.S. Pat. No. 7,563,284 in view of Stubstad U.S. Pat. No. 3,867,728).
Spinal Kinetics, Inc.'s Second Amended Preliminary Invalidity Contentions—Exhibit 28 (chart comparing claims of U.S. Pat. No. 7,429,270 to Baumgartner U.S. Pat. No. 5,370,697 in view of Stubstad U.S. Pat. No. 3,867,728 in further view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions—Exhibit 29 (chart comparing claims of U.S. Pat. No. 7,429,270 to Coppes U.S. Pat. No. 7,563,284 in view of Stubstad U.S. Pat. No. 3,867,728 further in view of Development and Characterization of a Prosthetic Intervertebral Disc, Hudgins, Georgia Inst. of Tech., Nov. 1998).
Burri et al., Neuentwicklung eines Implantates für den totalen Bandschiebenersatz, Vorgelegt von: Im Rahmen des Studiums für "Maschinenbau und Vergahrenstechnik" an der Eidgenöossischen Technischen Hochschule Zürich, im Feb. 2002).
English Translation of Burri et al., Neuentwicklung eines Implantates für den totalen Bandschiebenersatz, Vorgelegt von: Im Rahmen des Studiums für "Maschinenbau und Vergahrenstechnik" an der Eidgenöossischen Technischen Hochschule Zürich, im Feb. 2002), entitled Mechanical Engineering and Process Engineering at the Swiss Fedearl Institute of Technology Zurich (ETH Zurich) Feb. 2002.
Burri et al., Neuentwicklung eines lumbalen bewegungserhaltenden Bandscheibenimplantates, Feb. 25, 2002.
English Translation of Burri et al., Neuentwicklung eines lumbalen bewegungserhaltenden Bandscheibenimplantates, Feb. 25, 2002.
Hudgins, Development and Characterization of a Prosthetic Intervertebral Disc, Hudgins, Georgia Inst. of Tech., Nov. 1998.

(56) References Cited

OTHER PUBLICATIONS

Kweon et al., Optimal Design of Synthetic Intervertebral Disc Prosthesis Considering Nonlinear Mechanical Behavior, Dec. 20, 2001.

* cited by examiner

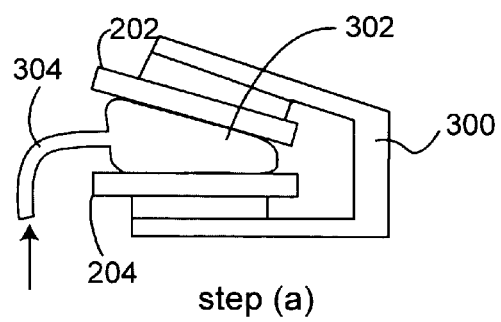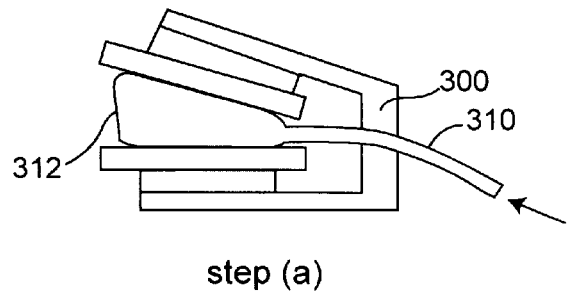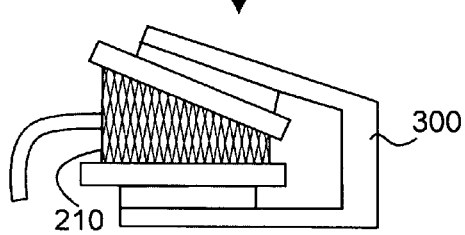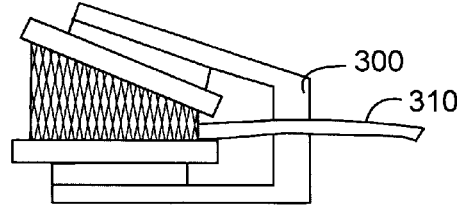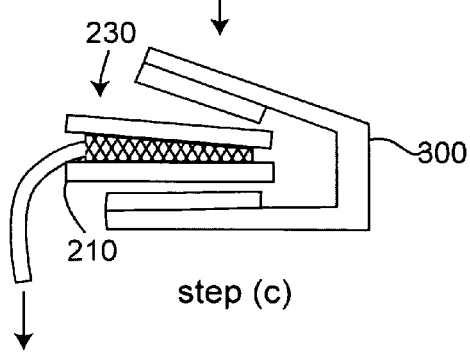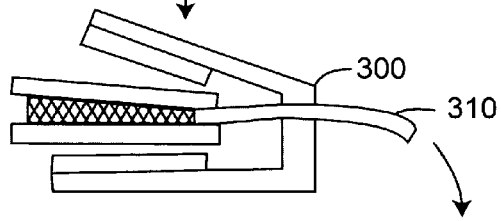
Fig. 4　　　　　　　　　Fig. 5

PROSTHETIC INTERVERTEBRAL DISCS HAVING BALLOON-BASED FILLABLE CORES THAT ARE IMPLANTABLE BY MINIMALLY INVASIVE SURGICAL TECHNIQUES

RELATED APPLICATIONS

This application claims benefit from U.S. provisional patent application No. 60/909,443, filed Mar. 31, 2007, the entirety of which is incorporated by reference.

FIELD

The described devices are spinal implants that may be surgically implanted into the spine to replace damaged or diseased discs using a posterior approach. The discs are prosthetic devices that approach or mimic the physiological motion and reaction of the natural disc.

BACKGROUND

The intervertebral disc is an anatomically and functionally complex joint. The intervertebral disc is composed of three component structures: (1) the nucleus pulposus; (2) the annulus fibrosus; and (3) the vertebral end plates. The biomedical composition and anatomical arrangements within these component structures are related to the biomechanical function of the disc.

The spinal disc may be displaced or damaged due to trauma or a disease process. If displacement or damage occurs, the nucleus pulposus may herniate and protrude into the vertebral canal or intervertebral foramen. Such deformation is known as herniated or slipped disc. A herniated or slipped disc may press upon the spinal nerve that exits the vertebral canal through the partially obstructed foramen, causing pain or paralysis in the area of its distribution.

To alleviate this condition, it may be necessary to remove the involved disc surgically and fuse the two adjacent vertebrae. In this procedure, a spacer is inserted in the place originally occupied by the disc and the spacer is secured between the neighboring vertebrae by the screws and plates or rods attached to the vertebrae. Despite the excellent short-term results of such a "spinal fusion" for traumatic and degenerative spinal disorders, long-term studies have shown that alteration of the biomechanical environment leads to degenerative changes particularly at adjacent mobile segments. The adjacent discs have increased motion and stress due to the increased stiffness of the fused segment. In the long term, this change in the mechanics of the motion of the spine causes these adjacent discs to degenerate.

Artificial intervertebral replacement discs may be used as an alternative to spinal fusion.

SUMMARY

Prosthetic intervertebral discs and methods for using such discs are described. The subject prosthetic discs include an upper end plate, a lower end plate, and a compressible core member disposed between the two end plates. The compressible core comprises an inflatable member or balloon filled with an elastomeric material or a hydrogel. The described prosthetic discs have shapes, sizes, and other features that are particularly suited for implantation using minimally invasive surgical procedures, particularly from a posterior approach.

In one variation, the described prosthetic discs include top and bottom end plates separated by one or more compressible core members. The two plates may be held together by at least one fiber wound around at least one region of the top end plate and at least one region of the bottom end plate. The described discs may include integrated vertebral body fixation elements. When considering a lumbar disc replacement from the posterior access, the two plates are preferably elongated, having a length that is substantially greater than its width. Typically, the dimensions of the prosthetic discs range in height from 8 mm to 15 mm; the width ranges from 6 mm to 13 mm. The height of the prosthetic discs ranges from 9 mm to 11 mm. The widths of the disc may be 10 mm to 12 mm. The length of the prosthetic discs may range from 18 mm to 30 mm, perhaps 24 mm to 28 mm. Typical shapes include oblong, bullet-shaped, lozenge-shaped, circular, rectangular, or the like The described disc prosthetic structures may be held together by at least one fiber wound around at least one region of the upper (or first) end plate and at least one region of the lower (or second) end plate. The fibers are generally high tenacity fibers with a high modulus of elasticity. The elastic properties of the fibers, as well as factors such as the number of fibers used, the thickness of the fibers, the number of layers of fiber windings in the disc, the tension applied to each layer, and the crossing pattern of the fiber windings enable the prosthetic disc structure to mimic the functional characteristics and biomechanics of a normal-functioning, natural disc.

A number of conventional surgical approaches may be used to place a pair of prosthetic discs. Those approaches include a modified posterior lumbar interbody fusion (PLIF) and a modified transforaminal lumbar interbody fusion (TLIF) procedures. We also describe apparatus and methods for implanting prosthetic intervertebral discs using minimally invasive surgical procedures. In one variation, the apparatus includes a pair of cannulae that are inserted posteriorly, side-by-side, to gain access to the spinal column at the disc space. A pair of prosthetic discs may then be implanted by way of the cannulae to be located between two vertebral bodies in the spinal column.

The prosthetic discs may be configured by selection of sizes and structures suitable for implantation by minimally invasive procedures.

Other and additional devices, apparatus, structures, and methods are described by reference to the drawings and detailed descriptions below.

BRIEF DESCRIPTION OF THE DRAWINGS

The Figures contained herein are not necessarily drawn to scale, with some components and features being exaggerated for clarity.

FIGS. 4 and 5 show the production of two variations of my prosthetic disc.

DETAILED DESCRIPTION

Described below are prosthetic intervertebral discs, methods of using such discs, apparatus for implanting such discs, and methods for implanting such discs. It is to be understood that the prosthetic intervertebral discs, implantation apparatus, and methods are not limited to the particular embodiments described, as these may, of course, vary. It is also to be understood that the terminology used here is only for the purpose of describing particular embodiments, and is not intended to be limiting in any way.

Insertion of the prosthetic discs may be approached using modified conventional procedures, such as a posterior lumbar interbody fusion (PLIF) or transforaminal lumbar interbody fusion (TLIF). In the modified PLIF procedure, the spine is approached via midline incision in the back. The erector spinae muscles are stripped bilaterally from the vertebral lamina at the required levels. A laminectomy is then performed to further allow visualization of the nerve roots. A partial facetectomy may also be performed to facilitate exposure. The nerve roots are retracted to one side and a discectomy is performed. Optionally, a chisel may then used to cut one or more grooves in the vertebral end plates to accept the fixation components on the prostheses. Appropriately-sized prostheses may then be inserted into the intervertebral space on either side of the vertebral canal.

In a modified TLIF procedure, the approach is also posterior, but differs from the PLIF procedure in that an entire facet joint is removed and the access is only on one side of the vertebral body. After the facetectomy, the discectomy is performed. Again, a chisel may be used to create on or more grooves in the vertebral end plates to cooperatively accept the fixation components located on each prosthesis. The prosthetic discs may then be inserted into the intervertebral space. One prosthesis may be moved to the contralateral side of the access and then a second prosthesis then inserted on the access side.

It should be apparent that we refer to these procedures as "modified" in that neither procedure is used to "fuse" the two adjacent vertebrae.

Figure 1:
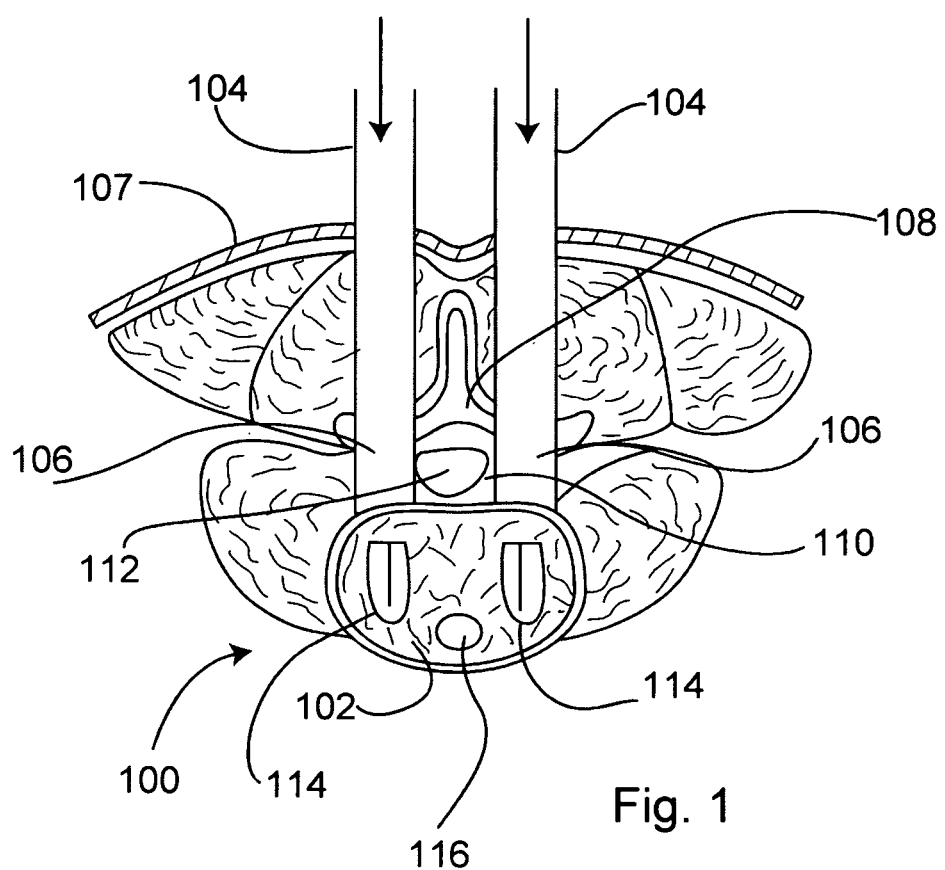
FIG. 1 shows a method for placement of prosthetic intervertebral discs using a posterior approach.

FIG. 1 shows a top, cross section view of a spine (100), sectioned across an intervertebral disc (102). This Figure depicts a minimally invasive surgical procedure for implanting a pair of intervertebral discs in an intervertebral region formed by the removal of a natural disc. This minimally invasive surgical implantation method is performed using a posterior approach, rather than the conventional anterior lumbar disc replacement surgery or the modified PLIF and TLIF procedures described above.

In FIG. 1, two cannulae (104) are inserted posteriorly, through the skin (107), to provide access to the spinal column. More particularly, a small incision is made and a pair of access windows created through the lamina (106) of one of the vertebrae (108) on each side of the vertebral canal (110) to access the natural vertebral disc. The spinal cord (112) and nerve roots are avoided or moved to provide access. Once access is obtained, the two cannulae (104) are inserted. The cannulae (104) may be used as access passageways in removing the natural disc with conventional surgical tools. Alternatively, the natural disc may be removed prior to insertion of the cannulae. The cannulae are also used to introduce the prosthetic intervertebral discs (114) to the intervertebral region.

The described prosthetic discs are of a design and capability such that they may be employed at more than one level, i.e., disc location, in the spine. Specifically, several natural discs may be replaced with my discs. As will be described in greater detail below, each such level will be implanted with at least two of my discs. Kits, containing two of my discs for a single disc replacement or four of my discs for replacement of discs at two levels in the spine, perhaps with sterile packaging are contemplated. Such kits may also contain one or more cannulae having a central opening allowing passage and implantation of my discs.

Once the natural disc has been removed and the cannulae (104) located in place, a pair of prosthetic discs (114) is implanted between adjacent vertebral bodies. The prosthetic discs have a shape and size suitable making them suitable for use with (or adapted for) various minimally invasive procedures. The discs may have a shape such as the elongated one-piece prosthetic discs described below.

A prosthetic disc (114) is guided through each of the cannula such that each of the prosthetic discs (114) is implanted between the two adjacent vertebral bodies. The two prosthetic discs (114) may be located side-by-side and spaced slightly apart, as viewed from above. Optionally, prior to implantation, grooves may be formed on the internal surfaces of one or both of the vertebral bodies in order to engage anchoring components or features located on or integral with the prosthetic discs (114). The grooves may be formed using a chisel tool adapted for use with the minimally invasive procedure, i.e., adapted to extend through a relatively small access space (such as the tunnel-like opening found in through the cannulae) and to chisel the noted grooves within the intervertebral space present after removal of the natural disc.

These discs may be used as shown in FIG. 1 or they may be implanted with an additional prosthetic disc or discs, perhaps in the position shown for auxiliary disc (116).

Additional prosthetic discs may also be implanted in order to obtain desired performance characteristics, and the implanted discs may be implanted in a variety of different relative orientations within the intervertebral space. In addition, the multiple prosthetic discs may each have different performance characteristics. For example, a prosthetic disc to be implanted in the central portion of the intervertebral space may be configured to be more resistant to compression than one or more prosthetic discs that are implanted nearer the outer edge of the intervertebral space. For instance, the stiffness of the outer discs (e.g., 114) may each be configured such that those outer discs exhibit approximately 5% to 80% of the stiffness of the inner disc, perhaps in the range of about 30% to 60% of the central disc (116) stiffness. Other performance characteristics may be varied as well.

This description may describe a number of variations of prosthetic intervertebral discs. By "prosthetic intervertebral disc" is meant an artificial or manmade device that is so configured or shaped that it may be employed as a total or partial replacement of an intervertebral disc in the spine of a vertebrate organism, e.g., a mammal, such as a human. The described prosthetic intervertebral discs have dimensions that permit them, either alone or in combination with one or more other prosthetic discs, to substantially occupy the space between two adjacent vertebral bodies that is present when the naturally occurring disc between the two adjacent bodies is removed, i.e., a void disc space. By "substantially occupy" is meant that, in the aggregate, the discs occupy at least about 30% by surface area, perhaps at least about 80% by surface area or more. The subject discs may have a roughly bullet or lozenge shaped structure adapted to facilitate implantation by minimally invasive surgical procedures.

The discs may include both an upper (or top) and lower (or bottom) end plate, where the upper and lower end plates are separated from each other by a compressible element such as one or more core members, where the combination structure of the end plates and compressible element provides a prosthetic disc that functionally approaches or closely mimics a natural disc. The top and bottom end plates may be held together by at least one fiber attached to or wound around at least one portion of each of the top and bottom end plates. As such, the two end plates (or planar substrates) are held to each other by one or more fibers that are attached to or wrapped around at least one domain, portion, or area of the upper end plate and lower end plate such that the plates are joined to each other.

Figure 2:
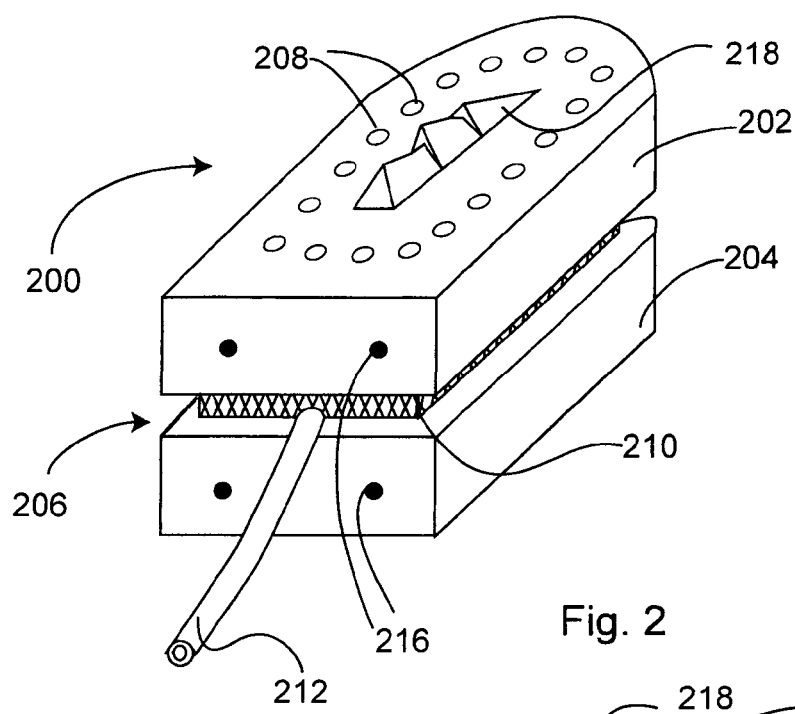
FIG. 2 is a perspective view of a variation of my prosthetic disc in a collapsed form.

FIG. 2 shows a perspective view of one variation of my prosthetic intervertebral disc (200) in a collapsed form. This variation comprises an upper end plate (202) and a lower end plate (204) separated by a compressible core (206). As discussed below in more detail, the compressible core (206) may comprise one or more inflatable core members (not shown) and be bounded by one or more fibers (210) extending between the upper end plate (202) and the lower end plate (204). Also shown in this Figure is inflation line (212) through which the inflation material may flow. The upper and lower end plates (202, 204) may include apertures (208), through which the fibers (210) may pass. Other components (woven or nonwoven fabrics, wires, etc.) may be used in functional substitution for the fibers (210).

Figure 3:
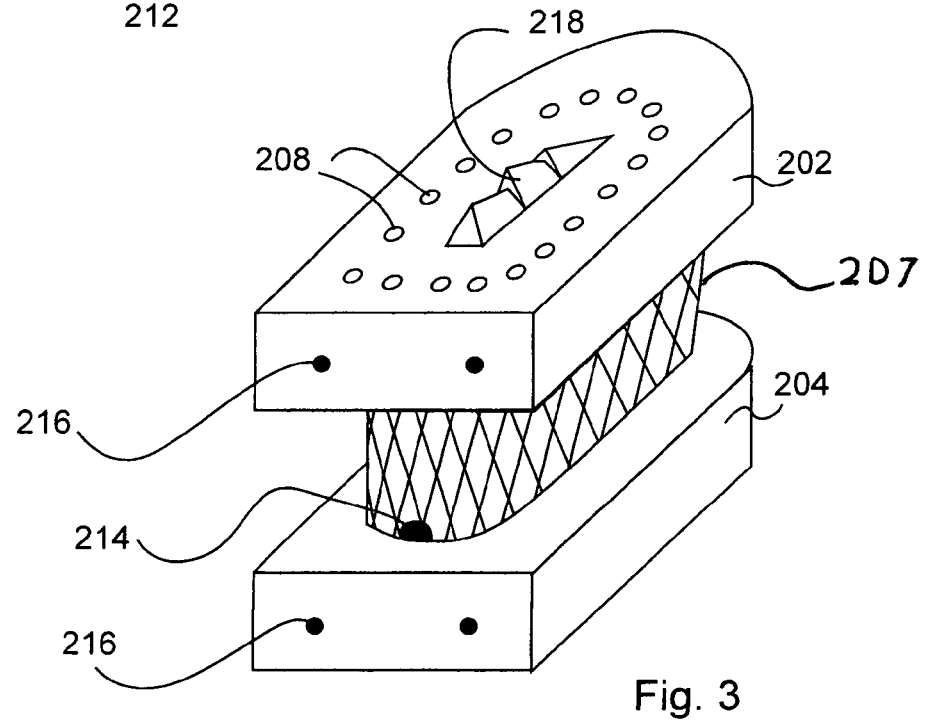
FIG. 3 is a perspective view of the FIG. 2 prosthetic disc in an inflated form.

FIG. 3 is a perspective view of the disc (200) shown in FIG. 2, but in an inflated, post-implantation condition. The fill line (212 in FIG. 2) has been removed and the balloon sealed (214). Shown in both FIGS. 2 and 3 are openings (216) useful in cooperative attachment with an implantation tool and attachment features or components (e.g., "keels") (218) for permanent attachment to vertebral bone.

The end plates are typically generally planar substrates having a length of from about 12 mm to about 45 mm, such as from about 13 mm to about 44 mm, a width of from about 11 mm to about 28 mm, such as from about 12 mm to about 25 mm, and a thickness of from about 0.5 mm to about 5 mm, such as from about 1 mm to about 3 mm. The top and bottom end plates are fabricated or formed from a physiologically acceptable material that provides for the requisite mechanical properties, primarily structural rigidity and durability. Representative materials from which the end plates may be fabricated are known to those of skill in the art and include, but are not limited to: metals such as titanium, titanium alloys, stainless steel, cobalt/chromium, etc.; plastics such as polyethylene with ultra high molar mass (molecular weight) (UHMW-PE), polyether ether ketone (PEEK), etc.; ceramics; graphite; etc.

The discs may also include fibers (207) wound between and connecting the upper end plate (202) to the lower end plate (204). These fibers (207) may extend through a plurality of openings or apertures (208) formed on portions of each of the upper and lower end plates (202, 204). Thus, a fiber (207) extends between the pair of end plates (202, 204), and extends up through a first aperture (208) in the upper end plate (202) and back down through an adjacent aperture (208) in the upper end plate (202). The fibers (207) may not be tightly wound, thereby allowing a degree of axial rotation, bending, flexion, and extension by and between the end plates. The amount of axial rotation generally is in the range from about 0° to about 15°, perhaps from about 2° to 10°. The amount of bending generally has a range from about 0° to about 18°, perhaps from about 2° to 15°. The amount of flexion and extension generally has a range from about 0° to about 25°, perhaps from about 3° to 15°. Of course, the fibers (207) may be more or less tightly wound to vary the resultant values of these rotational values. The balloon-based core members (not shown) forming compressible core (206) may be provided in a collapsed form for implantation.

An annular capsule may be included in the space between the upper and lower end plates (202, 204), surrounding the compressible core (206).

FIGS. 4 and 5 show step-wise construction of my prosthetic intervertebral discs. Specifically, FIG. 4, in step (a), shows a form (300) specifically constructed (size, angle, etc.) to produce a prosthetic disc that, when inflated, has the same angle between the upper end plate (202) and the lower end plate (204) as does the form (300). The upper end plate (202) and lower end plate are mounted on the form (300). A small balloon or inflatable member (302) having an inflation port and line (304) is selected to fit in the region between the upper and lower end plates (202, 204). In this version, the end plates are situated at an angle such that, when the fill line (304) is placed anteriorly, the resulting disc results in a lordotic angle between the adjacent vertebrae. The balloon is inflated with a generally inert gas (e.g., nitrogen, etc.) to an appropriate pressure. The balloons may generally be made from any appropriate polymer, but the materials used in making angioplasty or stent delivery balloons are quite good. Although materials used in making compliant and semicompliant balloons may be used in such balloons, polymeric materials used to make high pressure, noncompliant balloons are a better choice. Noncompliant balloons have typically been made of polyethyleneterephthalate (PET) with or without various other copolymers (e.g., polylactone). The balloon may comprise a member selected from the group consisting of polyamides, polyimides, polyolefins, and polyethylene-block amides. Multilayer balloons having significant puncture resistance are available.

With the balloon (302) inflated to size, as shown in step (b), the fibers (210) are then woven through the apertures (208 in FIGS. 2 and 3) to form a network of fibers that distribute force about the disc as force is applied to one of the end plates.

Finally, as shown in step (c), the balloon (302) with its associated fiber matrix (210) is deflated. The deflated disc (230) may be removed from the form (300). The disc (230) is ready for implantation. The deflated disc (230) may be compressed further before implantation.

FIG. 5 shows the same set of steps as in FIG. 4 with the exception that the fill line (310) is situated on the opposite side of the balloon (312).

Figure 6A:
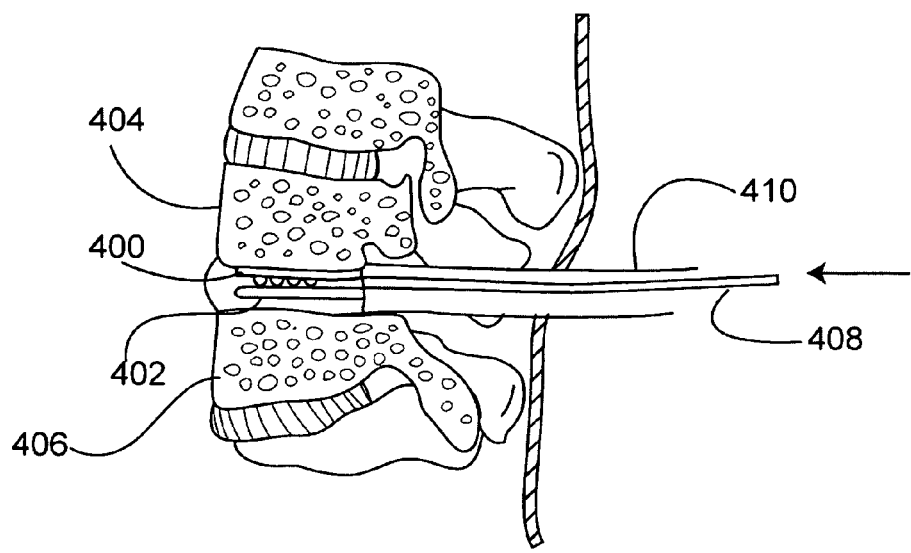
FIGS. 6A and 6B schematically illustrate a method for implanting the described prosthetic discs.

FIG. 6A shows placement of a deflated disc (400) into the intervertebral space (402) between an upper vertebra (404) and the adjacent lower vertebra (406). The placement tool with fill line (408) is shown schematically. The compressed disc (400) has been passed through the cannula (410) to the implantation site.

Figure 6B:
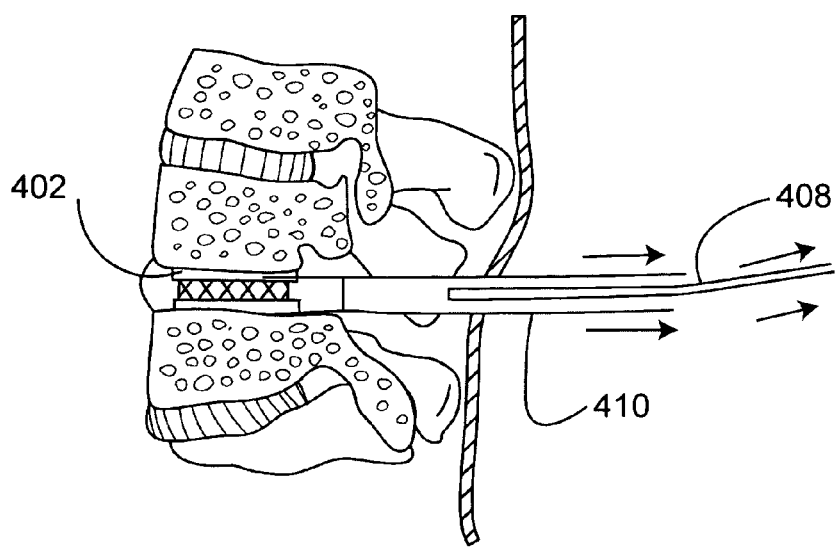

FIG. 6B shows the disc (402) after a filler material has been introduced into the balloon and the disc (402) inflated. The filler tube (408) is tied off or otherwise closed to prevent loss of filler into the body. Suitable filler materials are discussed below. The cannula (410) and the placement tool/filler line (408) are shown being removed.

Generically, at least two groups of materials are suitable as fillers for this balloon-based core: polymer systems that are curable after placement of the balloon to produce a compressible core and hydrogels. Physical mixtures of the two are also suitable.

The curable polymer system, for instance, may be a curable polyurethane composition comprising a number of components capable of being sterilized, stored, and mixed at the time of use to provide a flowable composition and initiate curing. The parts may include: (1) a prepolymer component comprising the reaction product of one or more polyols (e.g., polyether or polycarbonate polyols), and one or more diisocyanates, and optionally, hydrophobic additives, and (2) one or more curing components, e.g., one or more polyols, one or more chain extenders, one or more catalysts, and if desired, antioxidants and dyes. The composition, after mixing, will flow well enough to allow delivery to the balloon under pressure. These materials will also cure under physiological conditions.

Hydrogels are water-swellable or water-swollen polymeric materials typically having structures defined either by a crosslinked or an interpenetrating network of hydrophilic homopolymers or copolymers. In the case of physical crosslinking, the linkages may take the form of entanglements, crystallites, or hydrogen-bonded structures to provide structure and physical integrity to the polymeric network.

Suitable hydrogels may be formulated from a variety of hydrophilic polymers and copolymers including polyvinyl alcohol, polyethylene glycol, polyvinyl pyrrolidone, polyethylene oxide, polyacrylamide, polyurethane, polyethylene oxide-based polyurethane, and polyhydroxyethyl methacrylate, and copolymers and mixtures of the foregoing.

Silicone-base hydrogels are also suitable. Silicone hydrogels may be prepared by polymerizing a mixture of monomers including at least one silicone-containing monomer and or oligomer and at least one hydrophilic co-monomer such as N-vinyl pyrrolidone (NVP), N-vinylacetamide, N-vinyl-N-methyl acetamide, N-vinyl-N-ethyl acetamide, N-vinylformamide, N-vinyl-N-ethyl formamide, N-vinylformamide, 2-hydroxyethyl-vinyl carbonate, and 2-hydroxyethyl-vinyl carbamate (beta-alanine).

Each of the described prosthetic discs depicted in the Figures has a greater length than width. The aspect ratio (length:width) of the discs may be about 1.5 to 5.0, perhaps about 2.0 to 4.0, or about 2.5 to 3.5. Exemplary shapes to provide these relative dimensions include rectangular, oval, bullet-shaped, lozenge-shaped, and others. These shapes facilitate implantation of the discs by the minimally invasive procedures described above.

The surfaces of the upper and lower end plates, those surfaces in contact with and eventually adherent to the respective opposed bony surfaces of the upper and lower vertebral bodies, may have one or more anchoring or fixation components or mechanisms for securing those end plates to the vertebral bodies, e.g., (218) in FIGS. 2 and 3. The anchoring feature may be one or more "keels," a fin-like extension often having a substantially triangular cross-section and having a sequence of exterior barbs or serrations. This anchoring component is intended to cooperatively engage a mating groove that is formed on the surface of the vertebral body and to thereby secure the end plate to its respective vertebral body. The serrations enhance the ability of the anchoring feature to engage the vertebral body.

Further, this variation of the anchoring component may include one or more holes, slots, ridges, grooves, indentations, or raised surfaces to further assist in anchoring the disc to the associated vertebra. These physical features will so assist by allowing for bony ingrowth. Each end plate may have a different number of anchoring components, and those anchoring features may have a different orientation on each end plate. The number of anchoring features generally ranges in number from about 0 to about 500, perhaps from about 1 to 10. Alternatively, another fixation or anchoring mechanism may be used, such as ridges, knurled surfaces, serrations, or the like. In some variations, the discs will have no external fixation mechanism. In such variations, the discs are held in place laterally by the friction forces between the disc and the vertebral bodies.

Further, each of the described variations may additionally include a porous covering or layer (e.g., sprayed Ti metal) allowing boney ingrowth and may include some osteogenic materials.

As noted above, in the variations shown herein, the upper end plate and lower end plate may each contain a plurality of apertures through which the fibers may be passed through or wound, as shown. The actual number of apertures contained on an end plate is variable. Increasing the number of apertures allows an increase in the circumferential density of the fibers holding the end plates together. The number of apertures may range from about 3 to 100, perhaps in the range of 10 to 30. In addition, the shape of the apertures may be selected so as to provide a variable width along the length of the aperture. For example, the width of the apertures may taper from a wider inner end to a narrow outer end, or visa versa. Additionally, the fibers may be wound multiple times within the same aperture, thereby increasing the radial density of the fibers. In each case, this improves the wear resistance and increases the torsional and flexural stiffness of the prosthetic disc, thereby further approximating natural disc stiffness. In addition, the fibers may be passed through or wound on each aperture, or only on selected apertures, as needed. The fibers may be wound in a unidirectional manner, where the fibers are wound in the same direction, e.g., clockwise, which closely mimics natural annular fibers found in a natural disc, or the fibers may be wound bi-directionally. Other winding patterns, both single and multi-directional, may also be used.

The apertures provided in the various end plates discussed here, may be of a number of shapes. Such aperture shapes include slots with constant width, slots with varying width, openings that are substantially round, oval, square, rectangular, etc. Elongated apertures may be radially situated, circumferentially situated, spirally located, or combinations of these shapes. More than one shape may be utilized in a single end plate.

One purpose of the fibers is to hold the upper and lower end plates together and to limit the range-of-motion to mimic or at least to approach the range-of-motion of a natural disc. The fibers may comprise high tenacity fibers having a high modulus of elasticity, for example, at least about 100 MPa, perhaps at least about 500 MPa. By high tenacity fibers is meant fibers able to withstand a longitudinal stress of at least 50 MPa, and perhaps at least 250 MPa, without tearing. The fibers 140 are generally elongate fibers having a diameter that ranges from about 100 μm to about 1000 μm, and preferably about 200 μm to about 400 μm. The fibrous components may be single strands or, more typically, multi-strand assemblages. Optionally, the fibers may be injection molded or otherwise coated with an elastomer to encapsulate the fibers, thereby providing protection from tissue ingrowth and improving torsional and flexural stiffness. The fibers may be coated with one or more other materials to improve fiber stiffness and wear. Additionally, the core may be injected with a wetting agent such as saline to wet the fibers and facilitate the mimicking of the viscoelastic properties of a natural disc. The fibers may comprise a single or multiple component fibers.

The fibers may be fabricated from any suitable material. Examples of suitable materials include polyesters (e.g., Dacron® or the Nylons), polyolefins such as polyethylene, polypropylene, low-density and high density polyethylenes, linear low-density polyethylene, polybutene, and mixtures and alloys of these polymers. HDPE and UHMWPE are especially suitable. Also suitable are various polyaramids, poly-paraphenylene terephthalamide (e.g., Kevlar®), carbon or glass fibers, various stainless steels and superelastic alloys (such as nitinol), polyethylene terephthalate (PET), acrylic polymers, methacrylic polymers, polyurethanes, polyureas, other polyolefins (such as polypropylene and other blends and olefinic copolymers), halogenated polyolefins, polysaccharides, vinylic polymers, polyphosphazene, polysiloxanes, liquid crystal polymers such as those available under the tradename VECTRA, polyfluorocarbons such as polytetrafluoroethylene and e-PTFE, and the like.

The fibers may be terminated on an end plate in a variety of ways. For instance, the fiber may be terminated by tying a knot in the fiber on the superior or inferior surface of an end plate. Alternatively, the fibers may be terminated on an end plate by slipping the terminal end of the fiber into an aperture on an edge of an end plate, similar to the manner in which thread is retained on a thread spool. The aperture may hold the fiber with a crimp of the aperture structure itself, or by an additional retainer such as a ferrule crimp. As a further alternative, tab-like crimps may be machined into or welded onto the end plate structure to secure the terminal end of the fiber. The fiber may then be closed within the crimp to secure it. As a still further alternative, a polymer may be used to secure the fiber to the end plate by welding, including adhesives or thermal bonding. That terminating polymer may be of the same material as the fiber (e.g., UHMWPE, PE, PET, or the other materials listed above). Still further, the fiber may be retained on the end plates by crimping a cross-member to the fiber creating a T-joint, or by crimping a ball to the fiber to create a ball joint.

The annular capsule may be made of an appropriate polymer, such as polyurethane or silicone or the materials discussed above, and may be fabricated by injection molding, two-part component mixing, or dipping the end plate-core-fiber assembly into a polymer solution. The annular capsule may be oblong with straight sidewalls or with one or more bellows formed in the sidewalls. A function of the annular capsule is to act as a barrier that keeps the disc materials (e.g., fiber strands) within the body of the disc, and that keeps potential, natural in-growth outside the disc.

Where a range of values is provided, it is understood that each intervening value within the range, to the tenth of the unit of the lower limit (unless the context clearly dictates otherwise), between the upper and lower limit of that range and any other stated or intervening value in that stated range is described. The upper and lower limits of these smaller ranges may independently be included in the smaller ranges is also described, subject to any specifically excluded limit in the stated range. Where the stated range includes one or both of the limits, ranges excluding either or both of those included limits are also described.

Unless defined otherwise, all technical and scientific terms used herein have the same meaning as commonly understood by one of ordinary skill in the medical devices art. Although methods and materials similar or equivalent to those described here may also be used in the practice or testing of the described devices and methods, the preferred methods and materials are described in this document. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

As will be apparent to those of skill in the art upon reading this disclosure, each of the individual variations described and illustrated herein has discrete components and features which may be readily separated from or combined with the features of any of the other several embodiments without departing from the scope or spirit of this disclosure. For example, and without limitation, several of the variations described here include descriptions of anchoring features, protective capsules, fiber windings, and protective covers covering exposed fibers for integrated end plates. It is expressly contemplated that these features may be incorporated (or not) into those variations in which they are not shown or described.

All patents, patent applications, and other publications mentioned herein are hereby incorporated herein by reference in their entireties. The patents, applications, and publications discussed herein are provided solely for their disclosure prior to the filing date of the present application. Nothing herein is to be construed as an admission that contents of those patents, applications, and publications are "prior" as that term is used in the Patent Law.

The preceding merely illustrates the principles of the invention. It will be appreciated that those skilled in the art will be able to devise various arrangements which, although not explicitly described or shown herein, embody the principles otherwise described here and are included within its spirit and scope. Furthermore, all examples and conditional language recited herein are principally intended to aid the reader in understanding the described principles of my devices and methods. Moreover, all statements herein reciting principles, aspects, and variation as well as specific examples thereof, are intended to encompass both structural and functional equivalents. Additionally, it is intended that such equivalents include both currently known equivalents and equivalents developed in the future, i.e., any elements developed that perform the same function, regardless of structure.

What is claimed is:

1. A prosthetic intervertebral disc for inserting in an intervertebral space between two adjacent vertebrae in a spine, comprising:
   a.) a first end plate;
   b.) a second end plate;
   c.) at least one core member comprising a fillable noncompliant balloon having a first unfilled configuration and a second filled configuration, positioned between said first and second end plates; and
   d.) at least one fiber extending between and engaged with said first and second end plates; and
   wherein said end plates and said core member are held together by said at least one fiber and wherein the disc is configured to be insertable into the intervertebral space when the fillable noncompliant balloon is in the unfilled configuration and wherein the fillable noncompliant balloon is configured to be filled to the filled configuration after being inserted in the intervertebral space.

2. The prosthetic intervertebral disc of claim 1 wherein the fibers have been placed to extend between the first end plate and said second end plate in a form including the fillable noncompliant balloon.

3. The prosthetic intervertebral disc of claim 1 further including an amount of at least one curable polymer system, curable within the fillable noncompliant balloon.

4. The prosthetic intervertebral disc of claim 1 further including an amount of at least one hydrogel.

5. The prosthetic intervertebral disc of claim 1 wherein the fillable noncompliant balloon is a pre-formed balloon.

6. The prosthetic intervertebral disc of claim 1 wherein the fillable noncompliant balloon is a pre-shaped balloon.

7. The prosthetic intervertebral disc of claim 1 wherein the fillable noncompliant balloon comprises a balloon wall having a composition selected from the group consisting of polyamides, polyimides, polyolefins, and polyethylene-block amides.

8. A kit for surgically replacing a disc in a spine with a posterior approach, comprising exactly two of the prosthetic discs of claim 1.

9. The kit of claim 8 further comprising at least one cannula suitable for a posterior approach configured to access a disc to be replaced and to bypass the spinal cord and local nerve roots and further sized for passage of at least one of the prosthetic discs of claim 1.

10. The kit of claim 9 wherein the first and second end plates of each of the prosthetic discs have a length and a width, and wherein the length is greater than the width.

11. The kit of claim 10 wherein the first and second end plates of each of the prosthetic discs have a length:width aspect ratio range of about 1.5 to 5.0.

12. A kit for surgically replacing multiple discs in a spine with a posterior approach, comprising at least four of the prosthetic discs of claim 1.

13. The kit of claim 12 further comprising at least one cannula suitable for a posterior approach configured to access a disc to be replaced and to bypass the spinal cord and local nerve roots and further sized for passage of at least one of the at least four of the prosthetic discs of claim 1.

14. The kit of claim 13 wherein the first and second end plates of each of the at least four of the prosthetic discs have a length and a width, and wherein the length is greater than the width.

15. The kit of claim 14 wherein the first and second end plates of each of the at least four prosthetic discs have a length:width aspect ratio in the range of about 1.5 to 5.0.

16. A prosthetic intervertebral disc for inserting in an intervertebral space between two adjacent vertebrae in a spine, comprising:
   a.) a first end plate;
   b.) a second end plate;
   c.) at least one core member comprising a fillable noncompliant balloon having a pre-form or pre-shape, a first unfilled configuration, and a second filled configuration, the balloon being positioned between said first and second end plates; the pre-form or pre-shape providing a selected lordotic angle between the first end plate and the second end plate when the fillable noncompliant balloon is in the second filled configuration, and
   d.) at least one fiber extending between and engaged with said first and second end plates in a form including the fillable noncompliant balloon and placed to allow the fillable noncompliant balloon to form the selected lordotic angle between the first end plate and the second end plate when the fillable noncompliant balloon is in the second filled configuration; and
   wherein said end plates and said core member are held together by said at least one fiber and wherein the disc is configured to be insertable into the intervertebral space when the fillable noncompliant balloon is in the first unfilled configuration and wherein the fillable noncompliant balloon is configured to be filled to the second filled configuration after being inserted in the intervertebral space.

17. The prosthetic intervertebral disc of claim 16 further including an amount of at least one curable polymer system, curable within the fillable noncompliant balloon.

18. The prosthetic intervertebral disc of claim 16 further including an amount of at least one hydrogel.

19. The prosthetic intervertebral disc of claim 16 wherein the fillable noncompliant balloon comprises a balloon wall having a composition selected from the group consisting of polyamides, polyimides, polyolefins, and polyethylene-block amides.

20. A kit for surgically replacing a disc in a spine with a posterior approach, comprising exactly two of the prosthetic discs of claim 16.

21. The kit of claim 20 further comprising at least one cannula suitable for a posterior approach configured to access a disc to be replaced and to bypass the spinal cord and local nerve roots and further sized for passage of at least one of the prosthetic discs of claim 16.

22. The kit of claim 21 wherein the first and second end plates of each of the prosthetic discs have a length and a width, and wherein the length is greater than the width.

23. The kit of claim 22 wherein the first and second end plates of each of the prosthetic discs have a length:width aspect ratio in the range of about 1.5 to 5.0.

24. A kit for surgically replacing multiple discs in a spine with a posterior approach, comprising at least four of the prosthetic discs of claim 16.

25. The kit of claim 24 further comprising at least one cannula suitable for a posterior approach Configured to access a disc to be replaced and to bypass the spinal cord and local nerve roots and further sized for passage of at least one of the at least four of the prosthetic discs of claim 16.

26. The kit of claim 25 wherein the first and second end plates of each of the at least four of the prosthetic discs have a length and a width, and wherein the length is greater than the width.

27. The kit of claim 26 wherein the first and second end plates of each of the at least four prosthetic discs have a length:width aspect ratio in the range of about 1.5 to 5.0.

* * * * *